United States Patent [19]
Lepre

[11] Patent Number: 6,057,159
[45] Date of Patent: May 2, 2000

[54] PROCESSES FOR IDENTIFYING A SOLVENT CONDITION SUITABLE FOR DETERMINING A BIOPHYSICAL PROPERTY OF A PROTEIN

[75] Inventor: Christopher A. Lepre, Somerville, Mass.

[73] Assignee: Vertex Pharmaceuticals Incorporated, Cambridge, Mass.

[21] Appl. No.: 08/989,454

[22] Filed: Dec. 12, 1997

[51] Int. Cl.[7] .................................................. G01N 33/00
[52] U.S. Cl. ............................................................. 436/86
[58] Field of Search .................................. 436/8, 15, 17, 436/18, 86; 422/245

[56] References Cited

U.S. PATENT DOCUMENTS

| | | | |
|---|---|---|---|
| 4,886,646 | 12/1989 | Carter et al. | 422/245 |
| 5,096,676 | 3/1992 | McPherson et al. | 422/245 |
| 5,130,105 | 7/1992 | Carter et al. | 422/245 |
| 5,221,410 | 6/1993 | Kushner et al. | 156/600 |
| 5,270,452 | 12/1993 | Lim et al. | 530/399 |
| 5,400,741 | 3/1995 | DeTitta et al. | 117/206 |

OTHER PUBLICATIONS

Bagby, S. et al., "The Button Test: A Small Scale Method Using Microdialysis Cells for Assessing Protein Solubility at Concentrations Suitable for NMR", *Journal of Biomolecular NMR*, vol. 10, pp. 279–282 (1997).

Hofmann, A. et al., "A Sparse Matrix Screen to Establish Initial Conditions for Protein Renaturation", *Analytical Biochemistry*, vol. 230, pp. 8–15 (1995).

Jancarik, J. et al., "Sparse Matrix Sampling: Screening Method for Crystallization of Proteins", *Journal of Applied Crystallography*, vol. 24, pp. 409–411 (1991).

Matthews, S.J. et al., "The Use of Osmolytes to Facilitate Protein NMR Spectroscopy", *Journal of Biomolecular NMR*, vol. 3, pp. 597–600 (1993).

McPherson, A., "Current Approaches to Macromolecular Crystallization", *Eur. J. Biochem.*, vol. 189, pp. 1–23 (1990).

Santoro, M.M. et al., "Increased Thermal Stability of Proteins in the Presence of Naturally Occurring Osmolytes", *Biochemistry*, vol. 31, No. 23, pp. 5278–5283 (1992).

Scheim, C.H., "Solubility as a Function of Protein Structure and Solvent Components", *Biotechnology*, vol. 8, No. 4, pp. 308–317 (1990).

Wagner, G., "Prospets for NMR of large proteins", *Journal of Biomolecular NMR*, vol. 3, pp. 375–385 (1993).

Yancey, P.H. et al., "Living with Water Stress: Evolution of Osmolyte System", *Science*, vol. 217, pp. 1214–1222 (1982).

*Primary Examiner*—David A. Redding
*Attorney, Agent, or Firm*—Fish & Neave; James F. Haley, Jr.; Li Su

[57] ABSTRACT

The present invention provides processes for identifying a buffer condition suitable for determining a biophysical property of a protein. The processes of this invention utilize vapor diffusion means to alter buffer conditions, thus minimizing the volume of test samples and thereby conserving protein material. The processes of this invention are particularly useful to determine a buffer condition suitable for performing NMR studies on a protein.

9 Claims, 3 Drawing Sheets

PROCESSES FOR IDENTIFYING A SOLVENT CONDITION SUITABLE FOR DETERMINING A BIOPHYSICAL PROPERTY OF A PROTEIN

TECHNICAL FIELD OF THE INVENTION

The present invention provides processes for identifying a buffer condition suitable for determining a biophysical property of a protein. The processes of this invention utilize vapor diffusion means to alter buffer conditions, thus minimizing the volume of test samples and thereby conserving protein material. The processes of this invention are particularly useful to determine a buffer condition suitable for performing NMR studies on a protein.

BACKGROUND OF THE INVENTION

Elucidation of the biophysical properties of a protein in solution is a key to understanding its biological activity. Numerous techniques have been developed in the prior art to characterize a protein in solution. They include assays to determine functional activity, immunoreactivity and protein concentration, spectral methods such as Ultra-Violet, Visible, Infra-Red and fluorescence spectroscopy, Circular Dichroism, light scattering, surface plasma resonance, calorimetry, Nuclear Magnetic Resonance, High-Pressure Liquid Chromatography, gel electrophoresis, terminal sequencing analysis, and Mass Spectrometry. Such techniques typically monitor a biophysical property of the protein in solution, such as solubility, activity, ligand binding, aggregation state, and the conformation or folding state.

For example, spectral methods, such as Nuclear Magnetic Resonance (NMR), Circular Dichroism, fluorescence and absorbance spectroscopy provide detailed information regarding the secondary and tertiary structure of proteins in solution, changes in the behavior of a protein under different solvent conditions, comparison of properties between the protein and homologous or mutated forms of the protein, stability of the protein in solution, and structural transitions such as unfolding and refolding under a variety of conditions.

One of the major limitations in studying a biophysical property of a protein by the above techniques is the solubility and stability of the protein in solution. For example, NMR studies of proteins typically require a concentrated protein solution that is stable enough for acquisition of data for several days of more. This requirement has proven to be extremely difficult to satisfy on a consistent basis, and many NMR studies have been delayed or abandoned because of inability to stabilize or solubilize the protein of interest. This factor is likely to become more of a limitation in the future as NMR spectroscopists attempt to study larger proteins.

Typically, a solvent condition for a protein comprises a buffer system that maintains the pH of the solution at or near a constant value and, optionally, contains stabilizers such as salt, detergent, glycerol and excess reductant. The solvent condition in a protein solution is more commonly described as the buffer condition because a solution containing a protein almost always contains a buffer system.

At present, the main approach for identifying buffer conditions for studying the biophysical properties of a protein consists of transferring the protein at relatively low concentration into solutions with various buffer and pH conditions, and then concentrating the solutions and assessing the solubility and stability. Once a buffer and pH have been identified in which the protein is soluble and reasonably stable, an empirical approach is taken to varying stabilizers such as salt, reducing agents, glycerol, detergents, etc., in order to maximize solubility and stability.

In addition to enhancing solubility and stability, a stabilizer should not interfere with the technique employed to study the biophysical property. For example, if a protein solution is to be studied by NMR spectroscopy, then any stabilizer present in the solution should not give rise to resonances that interfere with the NMR spectrum. As another example, if a protein solution is to be studied by ultra-violet absorbance spectroscopy, then any stabilizer present in the protein solution should not strongly absorb ultra-violet radiation in the same frequency range as the protein.

The empirical approach for identifying appropriate buffer conditions is inefficient because the step of transferring the protein into various buffer systems is tedious and time-consuming. Moreover, sampling all of the possible combinations of buffer conditions consumes large amounts of valuable protein.

This is a crucial limitation for proteins that are extremely difficult to isolate and purify.

Thus, there is a need for a method to rapidly and efficiently identify a buffer condition in which a protein is soluble and stable. Such a buffer condition would be highly suitable for determining a biophysical property of a protein in solution using any one of the known techniques.

X-ray crystallographers have long had to contend with the converse problem in identifying conditions for precipitating a protein out of solution in order to grow crystals. Currently, the technique of vapor diffusion [1] is used to carry out controlled precipitation, and is combined with incomplete factorial [2] or sparse matrix [3] methods in order to screen large matrices of solvent conditions.

In a typical vapor diffusion method, a protein solution is combined with a precipitating agent and the mixture is sealed within a chamber containing a solvent reservoir in such a way that the solvent is gradually drawn out of the protein solution, leading to supersaturation and precipitation of the protein crystal.

The present invention provides a process for identifying buffer conditions that are suitable for determining a biophysical property of a protein in solution. The process of the present invention uses vapor diffusion, but differs from the crystal growing technique discussed above in that the absence of precipitants and the optional presence of stabilizers allows the optimization of solubility instead of insolubility.

SUMMARY OF THE INVENTION

The present invention provides a process for identifying a buffer condition suitable for carrying out a study for determining a biophysical property of a protein.

The process of this invention comprises the steps of:

a. providing a protein dissolved in a first buffer condition;

b. modifying said first buffer condition to a second buffer condition through vapor diffusion means; and c. evaluating the suitability of said second buffer condition for determining the biophysical property of the protein.

The process of this invention can be utilized to either concentrate or dilute a protein in solution, as well as to test the behavior of a protein in different concentrations of buffering salts and other pH-maintaining reagents, other salts and/or stabilizers. Different types of conditions are desirable depending upon the biophysical property of the protein to be determined. The processes of the present invention advantageously allow numerous different buffer conditions to be tested without wasting large amounts of potentially precious protein during the testing process.

DETAILED DESCRIPTION OF THE INVENTION

Figure 1A:
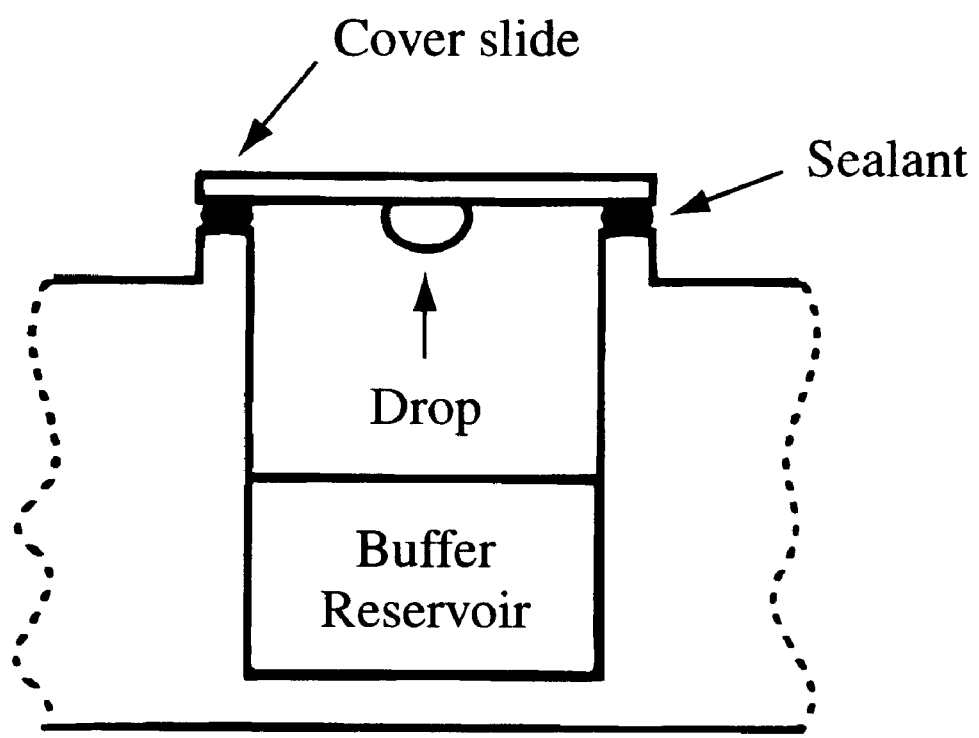
FIG. 1A is a cross-section view of the apparatus used for the hanging-drop method of the present invention.
Figure 1B:
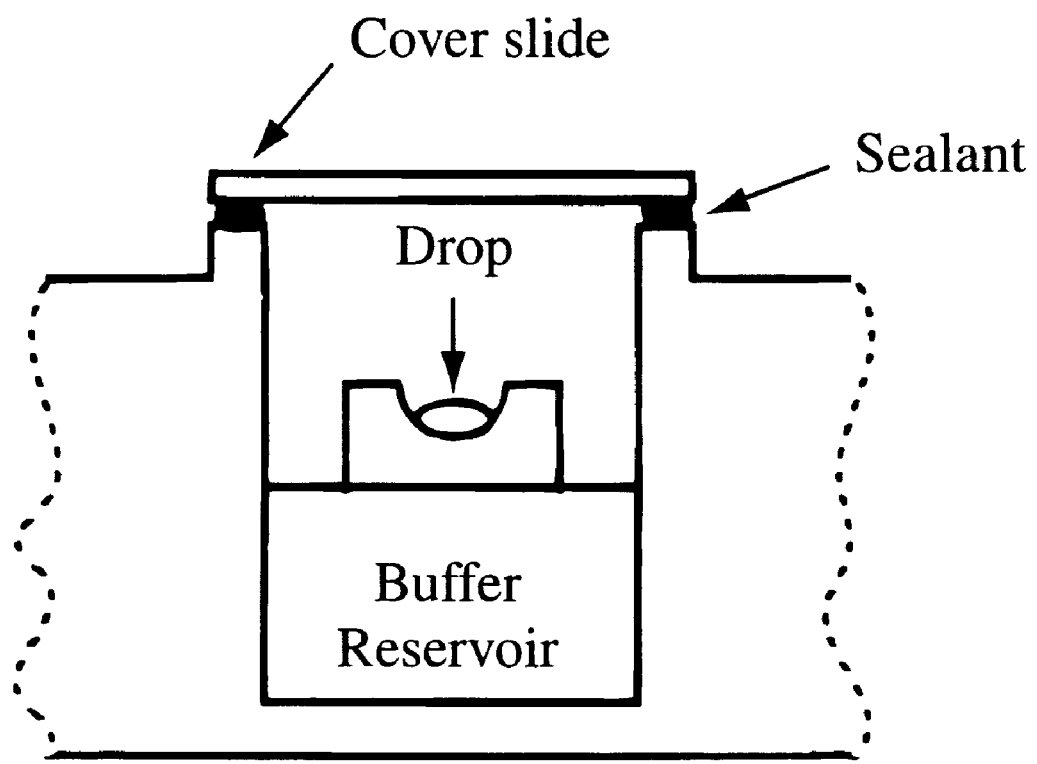
FIG. 1B is a cross-section view of the apparatus used for the sitting-drop method of the present invention.
Figure 1C:
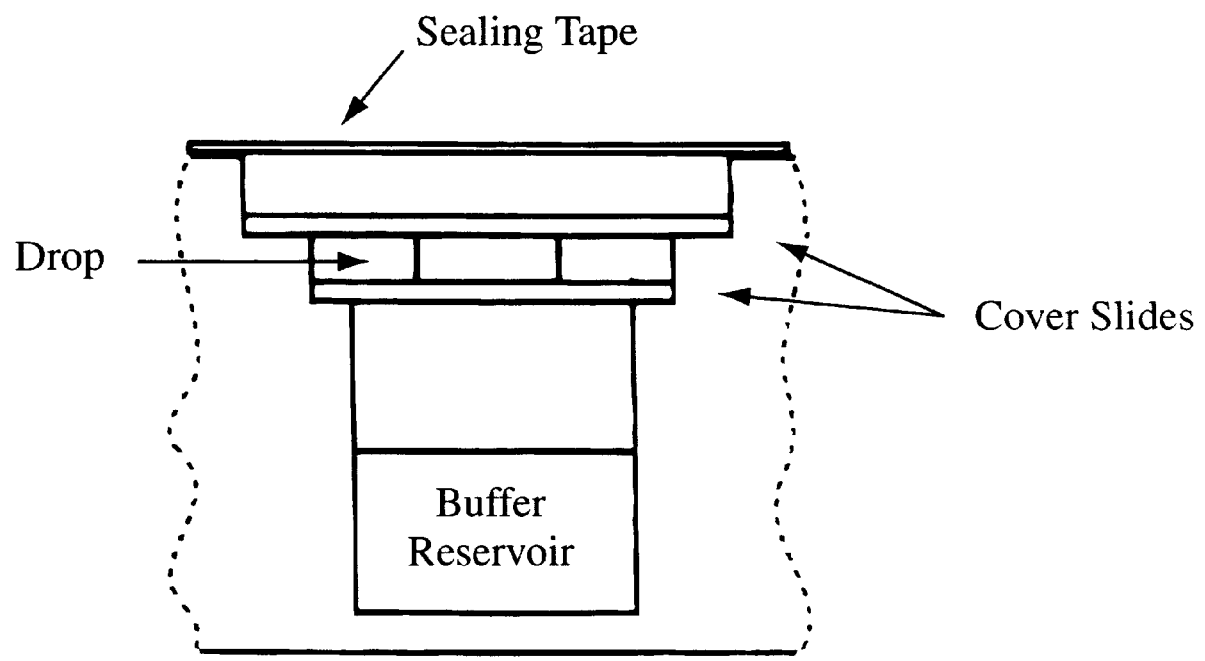
FIG. 1C is a cross-section view of the apparatus used for the sandwich-drop method of the present invention.

In order that the invention herein described may be more fully understood, the following detailed description is set forth. In the description, the following abbreviations are used:

NMR—Nuclear Magnetic Resonance
MES—[2-(N-morpholino)ethanesulfonic acid]
HEPES—N-2-hydroxyethylpiperazine-N-2
TRIS—[tris-(hydroxymethyl)-aminomethane]
DMSO—dimethyl sulfoxide
CHAPS—3[(3-cholamidopropyl) dimethylammonio]-1-propanesulfonate
BOG—n-hexyl-b-D-glucopyranside
ACES—(N-2-acetamido-2-aminoethane-sulfonic acid)
BES—[N,N-bis-(2-hydroxyethyl)-2
Bicine—[N,N-bis-(2-hydroxyethyl)-glycine]
BIS-Tris—{[bis-(2-hydroxyethyl)-imino]-tris-(hydroxymethyl)-methane}
BIS-Tris-propane—{1,3-bis-[tris-(hydroxylmethyl)-methylamino]-propane}
CAPS—[3-(cyclohexylamino)-propane-sulfonic acid]
CHES—[2-(N-cyclohexylamino) ethanesulfonic acid]
HEPES—(N-2-hydroxyethylpiperazine-N'-2-ethanesulfonic acid)
MES—[2-(N-morpholino) ethanesulfonic acid]
MOPS—[3-(N-morpholino) propanesulfonic acid]
PIPES—[piperazine-N,N'-bis-)2-ethanesulfonic acid]
TAPS—(3-{[tris-(hydroxymethyl)-methyl]-amino}-propanesulfonic acid)
TES—(2-{[tris-(hydroxymethyl)-methyl]-amino}-ethanesulfonic acid)
Tricine—{N-{tris-(hydroxylmethyl-methyl]-glycine}

The present invention provides a process for identifying a buffer condition suitable for determining a biophysical property of a protein. According to one embodiment, the process comprises the steps of:

a. providing a protein dissolved in a first buffer condition;

b. modifying said first buffer condition to a second buffer condition through vapor diffusion means; and c. evaluating the suitability of said second buffer condition for determining the biophysical property of the protein.

The term "buffer condition", as used herein denotes a solution capable of maintaining the pH at or near a constant value. A buffer condition comprises a solvent, a reagent capable of maintaining pH, and the protein dissolved therein. Additional components, such as a stabilizer, may also be present in a buffer condition if they are necessary.

Buffer conditions for proteins are well known in the art, and typically comprise water as a solvent and an acid-base conjugate pair to maintain pH. Organic solvents and other volatile solvent may also be utilized, but are less desirable.

Reagents capable of maintaining pH that are useful in the buffer conditions of the present invention include, but are not limited to, potassium phosphate, sodium phosphate, sodium acetate, sodium citrate, ammonium acetate, cacodylic acid, imidazole, boric acid, bicine, ACES, BES, BIS-Tris, BIS-Tris-propane, CAPS, CHES, glycine amide, glycylglycine, MES, MOPS, PIPES, HEPES, TAPS, TES, tricine, triethanolamine, or TRIS. Preferred pH-maintaining reagents are potassium phosphate, sodium phosphate, sodium acetate, ammonium acetate, cacodylate, imidazole, bicine, BIS-Tris, sodium citrate, imidazole, MES, MOPS, PIPES, HEPES, triethanolamine, or TRIS.

According to one embodiment, the process of the present invention comprises the first step of providing a desired protein dissolved in a first buffer condition. This step may be achieved in a number of ways. For example, a protein may be directly dissolved in the first buffer condition.

Alternatively, the protein may be dissolved initially in a solution that contains some, but not all, of the components of the first buffer condition. Once the protein is dissolved in such a solution, the remaining first buffer condition components may then be added to the protein solution, either from concentrated solution stocks or as solids. Yet another method for providing a protein dissolved in a first buffer condition is to first dissolve the protein in a solution and then dialyze that protein solution against another solution, such that upon completion of dialysis, the protein is dissolved in the first buffer condition. Other alternatives to direct dissolution of the protein into the first buffer condition include initial dissolution of the protein into a solution followed by buffer exchange into the first buffer condition using gel filtration, centrifugal filtration, or ultrafiltration methods, all of which are well known in the art.

Preferably, the first buffer condition comprises a minimum concentration of the components (i.e., pH-maintaining reagents, stabilizers) that are capable of maintaining the pH at or near a constant value and of keeping the protein dissolved.

Stabilizers may also be utilized in the first buffer condition when dissolution of the protein is otherwise difficult. Stabilizer which may be useful in the methods of this invention include salts, reducing agents, detergents, glycerol, polyols, osmolytes, chaotropes, organic solvents, electrostatic reagents, metal ions, ligands, inhibitors, cofactors or substrates, chaperonins, redox buffers, disulfide isomerases and protease inhibitors.

Typically, it is desirable that the stabilizer concentration in the first buffer condition is kept low in order to avoid potential problems. For example, a large excess of reducing agents may reduce structurally important disulfide bonds; glycerol viscosity effects may induce unacceptable line broadening in NMR spectroscopy; and detergents may form micelles above a critical concentration.

The second step in the method of this invention is the modification of the first buffer condition into a second buffer condition which is achieved through vapor diffusion means. The second buffer condition differs from the first buffer condition in any or all of the following features: changes in the concentration of the protein, changes in the concentration of reagents that maintained pH in the first buffer condition, changes in the concentration of stabilizers that may have been present in the first buffer system, and changes in pH. The transfer of solvent due to vapor diffusion modifies the first buffer condition to a second buffer condition.

According to one embodiment of the present invention, the vapor diffusion means for modifying the first buffer condition consists of a physically closed system first comprising a chamber containing a reservoir solution and a vessel that holds the protein dissolved in the first buffer condition.

The vessel that holds the protein dissolved in the first buffer condition may be a cuvette, a test tube, a multi-well plate, or any other suitable vessel. Alternatively, the vessel may be a slide or cover slip which has a surface tension sufficient to keep a droplet of protein dissolved in the first buffer condition attached to its surface even when the vessel is inverted ("hanging drop").

The reservoir solution comprises a solvent. That solvent may be either aqueous or organic in nature. The solvent may further comprise any or all of the following dissolved therein: acid or base, salts, pH-maintaining reagents, and stabilizers.

The reservoir solution must also have a vapor pressure sufficient to allow vapor diffusion of a solvent between the reservoir solution and the first buffer condition. As will be apparent to those in the art, the vessel containing the first buffer condition must be physically positioned with respect to the reservoir solution so as to allow vapor diffusion to occur. This is preferably achieved by forming a closed system comprising the reservoir in close physical proximity to the vessel holding the first buffer condition.

Vapor diffusion techniques known in the prior art can be readily employed in the processes of the present invention. Such techniques include, but are not limited to, the hanging drop method, the sitting drop method and the sandwich-drop method.

For example, in the hanging-drop method, a protein solution in a first buffer condition, typically 0.5–8 mL by volume, is placed on a glass slip. The glass slip is then inverted and sealed onto a well containing a reservoir buffer solution having a vapor pressure different from that of the protein solution. A schematic of a typical apparatus for the hanging-drop method is shown in FIG. IA. The exposure to the reservoir solution results in vapor diffusion of solvent into or out of the protein solution. This diffusion modifies the first buffer condition of the protein solution to a second buffer condition.

In the sitting-drop method, a drop of protein solution in a first buffer condition, typically up to approximately 200 mL by volume, is placed on a plate having a depression to hold the protein solution. The plate is then placed in a chamber and exposed to a reservoir buffer solution having a vapor pressure different from that of the protein solution. A schematic of a typical apparatus for the sitting-drop method is shown in FIG. IB. The exposure to the reservoir buffer solution results in vapor diffusion of solvent into or out of the protein solution. This diffusion modifies the first buffer condition of the protein solution to a second buffer condition.

In the sandwich-drop method, a drop of protein solution is sandwiched between two glass plates and sealed in a chamber containing a reservoir solution having a vapor pressure different from that of the protein solution. A schematic of a typical apparatus for the sandwich-drop method is shown in FIG. IC. The exposure to the reservoir buffer solution results in vapor diffusion of solvent into or out of the protein solution. The diffusion modifies the first buffer condition of the protein solution to a second buffer condition. Those of skill in the art will recognize that salts and pH-maintaining reagents will be the main contributors to the osmolarity of the various solutions and buffer conditions utilized in this invention. This is because these reagents will normally be present in much higher concentration than the protein or other stabilizers.

According to one embodiment, the solvent in the reservoir solution vapor diffuses into the protein solution with the first buffer condition, thereby increasing the amount of solvent in the protein solution; i.e., diluting the components present in the first buffer condition. Such a dilution occurs when the osmolarity of the first buffer system is lower than that of the reservoir solution.

The dilution method is particularly useful for identifying alternate stabilizers ("test" stabilizers) for proteins that have heretofore required the presence of a chaotrope or a high concentration of stabilizer—both of which were undesirable for studying a biophysical property of the protein. The desired test stabilizer is one that stabilizes the protein without precipitating it, while being present in low enough concentration to not interfere with subsequent studies of a biophysical property of the protein.

This may be carried out by creating first buffer conditions through the addition of different "test" stabilizers and/or different amounts of "test" stabilizers to protein solutions containing the undesirable chaotrope or stabilizer. The resulting plurality of first buffer conditions are then exposed to a low osmolarity reservoir solution under conditions which allow solvent to diffuse into the protein solution. This creates a second buffer condition wherein the concentration of the undesirable chaotrope or stabilizer is reduced to below the level normally needed to keep the protein soluble. Each second buffer condition is then analyzed to determine if the "test" stabilizer is effective in keeping the protein soluble. The solubility of the protein in the second buffer condition can be readily determined by examining each drop for clarity and an absence of precipitate. If the protein remains soluble in the second buffer condition, one may then perform tests to determine whether additional biophysical properties of the protein can be assayed in that second buffer condition.

Because the dilution method described above uses small volumes of protein solution (as little as 10 to 100 ul), the method can be readily extended to a batch screening method using a 96-well microtiter plate. Each of the 96 wells in the plate is filled with a drop of protein solution having a different first buffer condition (varying types and concentration of "test" stabilizer). The plate is then subjected to vapor diffusion in the presence of a reservoir solution. The advantage of using a microtiter plate is that it lends itself readily to automation of the solubility assay.

In addition to screening the efficacy of new stabilizers, the effect of changing the pH of the protein solution may also be readily evaluated by the dilution method. In such a case, the reservoir solution contains a volatile acid or base. As the acid or the base diffuses into the drop of protein solution, it creates a second buffer condition having a decreased or increased pH, respectively.

According to another embodiment, solvent diffuses out of the first buffer condition into the reservoir solution, thus creating a second buffer condition wherein the reagents contained in the first buffer condition have a higher concentration. Such a diffusion of solvent occurs when the osmolarity of the first buffer system is less than that of the reservoir solution.

This concentration method may be employed to simultaneously test a plurality of second buffer conditions to determine in which one a protein is most soluble. For example, in one particular embodiment individual aliquots (preferably less than 100 $\mu$l and more preferably less than 10 $\mu$l) of a protein solution are combined with different pH-maintaining reagents and/or stabilizers to create a plurality of first buffer conditions. Thus, the various first buffer conditions may differ from each other in the concentration of protein, the type or concentration of pH-maintaining reagents, the pH, and/or the type or concentration of stabilizer.

Each of the plurality of first buffer conditions is then exposed to a reservoir solution of higher osmolarity under conditions which allow solvent to diffuse out of the first buffer conditions into the reservoir solution. This modifies the first buffer condition of each protein solution to a second buffer condition wherein the concentration of protein (and the other reagents) is increased.

For example, the vapor diffusion method described above can be carried out by the hanging drop method using a Linbro plate with 24 wells. Thus, 24 first buffer conditions, each differing in the buffer type or concentration, protein concentration, pH, and/or stabilizer type or concentration, are prepared and a drop of each is placed on a separate glass cover slip. In a preferred embodiment, the particular pH-maintaining reagents in the reservoir solution and the first buffer condition are the same, although the concentration of those reagents is lower in the first buffer condition.

Each well is then partially filled with a reservoir solution having a higher osmolarity than the first buffer condition. The glass cover slip containing the first buffer condition is then inverted and sealed onto the well containing the corresponding reservoir buffer. The plate is then left undisturbed to allow vapor diffusion to occur, and the buffer conditions of each of the 24 drops is modified to a second buffer condition.

If the pH-maintaining reagents in the reservoir solution and the first buffer condition are identical, but lower in concentration in the latter, solvent will diffuse out of each drop until the total concentration of buffer in the drop is approximately the same as the concentration in the reservoir (assuming that the pH-maintaining reagents are the main contributor to the osmolarity of both the reservoir solution and the first buffer condition).

The concentration of the protein in the drop in the second buffer condition (i.e., after vapor diffusion has reached equilibrium) is controlled by the ratio of the protein and buffer solutions in the drop. For example, two volumes of protein solution are combined with one volume of reservoir solution to create the first buffer condition. Thus, in the first buffer condition, the concentration of reservoir solution components is ⅓ that in the reservoir solution itself. The concentration of protein in the first buffer condition is ⅔ of what it was in the original protein solution. Following vapor diffusion, the concentration of both the protein and the reservoir solution components in the second buffer condition will be 3 times greater than they were in the first buffer condition. Thus, the concentration of protein in the second buffer condition will be approximately twice the concentration of the original protein solution (⅔×3).

This embodiment allows one to start with a dilute protein solution, and then increase the concentration to a level at which the protein is not soluble in the original protein solution. In this way, it is possible to readily assess the ability of different buffer conditions to increase the protein solubility above that achieved in an original protein solution.

For increased efficiency, it is preferable to test several different protein concentrations in each well by placing multiple drops, each with a different ratio of protein and buffer solutions, onto each glass slip.

A 24-well plate may be prepared using only 1–2 mL drops of a protein solution. This method thus affords a rapid screening of numerous buffer conditions using a minimum amount of protein.

Alternatively, vapor diffusion on a plurality of protein solutions may be carried out using the sitting drop method or the sandwich drop method. Vapor diffusion apparati used in the prior art for growing crystals simultaneously in a plurality of protein solutions may be readily employed in the processes of the present invention. Such apparatus are disclosed in, for example, U.S. Pat. Nos. 4,886,646, 5,096,676, 5,130,105, 5,221,410 and 5,400,741, the disclosure of which are herein incorporated by reference.

Alternatively, after combination with various buffer solutions each of the drops may be allowed to undergo vapor diffusion with a common reservoir solution.

According to yet another embodiment, the process of vapor diffusion may be repeated wherein the reservoir buffer is replaced with a buffer of higher osmolarity and the second buffer condition is modified to a third buffer condition using vapor diffusion means. This can achieve, for example, a stepwise concentration of protein. In yet another embodiment, this process may be repeated additional times by successively replacing the reservoir buffer with more concentrated solutions and subjecting each vapor-diffusion equilibrated drop to that new reservoir solution.

According to another embodiment, a volatile acid or base may be added to the reservoir solution. Diffusion of the acid or base into the drops modifies the pH of the second buffer condition as compared to the first buffer condition.

Following vapor diffusion, the suitability of the second buffer condition for biophysical studies depends on the biophysical property to be determined and the technique employed for that determination. Biophysical properties of a protein according to this invention include solubility, biological activity, conformation and aggregation or folding state. The term "biophysical property", as used herein, refers only to a property that is measured when a protein is in solution. Thus, that term, specifically excludes techniques such as X-ray crystallography, wherein the protein is in an insoluble state.

For example, if the three dimensional structure of a protein is being analyzed by NMR or another spectral method, then the protein should have high solubility in the second buffer condition. Using the process of the present invention, a multitude of second buffer conditions may be rapidly and efficiently screened for solubility of the protein.

The solubility of the protein in the second buffer condition can examined by known techniques in the prior art. For example, the solubility may be examined by visual inspection of the protein solution for cloudiness or precipitate. The solubility may be also be examined semi-quantitatively using a microscope by estimating the surface area of the protein solution that is covered by protein precipitate. After examining different second buffer conditions, a pattern of relative solubility and stability will typically emerge.

If the protein is soluble over a broad range of second buffer conditions, making it difficult to identify the most solubilizing conditions, then a "torture test" may be carried out by varying the temperature of the second buffer conditions; the less stable or soluble samples will precipitate first. Alternatively, a similar test may be carried out by successively increasing the osmolarity of the reservoir solutions following vapor diffusion and re-subjecting the drop to vapor diffusion in order to further concentrate the protein solutions.

Similarly, buffer conditions suitable for activity assays may be identified using the processes of the present invention. For example, 20 mL drops of a protein solution, each drop having a different first buffer condition, can be screened in batches of 24 using a 24-well plate by the sitting-drop method. From an examination of the drops after vapor diffusion, the second buffer conditions that are conducive to solubilizing the protein can be identified by examining the drops for clarity or lack of a precipitate. From each 20 mL drop exhibiting protein solubility, aliquots of 1 mL or less of protein solution may be prepared and tested for activity. This will allow the identification of the buffer condition suitable for activity assays.

Buffer conditions suitable for determining the aggregation state of a protein in a solution may be readily identified using the processes of the present invention. For example, 20 mL drops of a protein solution, each drop having a different first buffer condition, can be screened in batches of 24 using a 24-well plate by the sitting-drop method. After vapor diffusion, the second buffer conditions may be analyzed in a dynamic light scattering instrument to determine the aggregation state of the protein.

In spectral techniques, such as NMR, it is desirable for the protein aggregation state to be monodisperse. In addition, the preparation of crystals for x-ray crystallographic analysis also requires a concentrated protein solution, and monodisperse protein is more likely than polydisperse protein to form high quality crystals. The present invention may be used to identify buffer conditions in which a concentrated, monodisperse protein solution may be prepared prior to carrying out a crystallization using prior art crystallographic vapor diffusion methods. Thus, the above process allows a rapid identification of buffer conditions that are conducive for preparing monodisperse samples for spectral and crystallographic analysis.

The biophysical properties of a protein may be analyzed by applying multiple methods to the same drops. For example, 20 mL drops of different first buffer conditions can be screened in batches of 24 using a 24-well plate by the sitting-drop method. After vapor diffusion, the second buffer condition drops may be evaluated for solubility of the protein therein using visual examination, followed by dynamic light scattering to determine aggregation state, and an assay to measure functional activity.

It will, thus, be seen that processes for identifying a second buffer condition suitable for determining a biophysical property of a protein have been provided. One skilled in the art will appreciate that the present invention can be practiced by other than the described embodiments, which are presented for purposes of illustration and not of limitation.

EXAMPLE 1

$^{15}$N labeled human recombinant glia maturation factor (GMF-b) with an amino-terminal His$_6$ tag (24 kDa) was expressed in E. coli using minimal media and purified using metal affinity resin at a yield of 30 mg purified protein per liter media (Chambers, S.; Fulghum, J.; Lepre, C., unpublished results). After refolding (Kaplan et al. 1991), the protein was exchanged into 50 mM potassium phosphate buffer at pH 7.4. Prior to solvent optimization, the maximum concentration that could be achieved was 8 mg/ml (330 mM).

After exchange into 10 mM potassium phosphate buffer, a hanging drop pH screen was set up using a 24-well Linbro plate with siliconized glass cover slips. The reservoir volume was 1 ml of different 100 mM buffer solutions at varying pH (see Table 1 below for details), and the first buffer condition consisted of 2 ul of protein solution mixed with 1 ul of 100 mM reservoir buffer (final equilibrium concentration around 16 mg/ml). A total of 0.384 mg of protein was used.

Following vapor diffusion 24 hours at room temperature, the amount of precipitate in the drops of second buffer condition was measured by placing the trays against a black background, illuminating them from the side, and visually examining each drop under a microscope. Under these lighting conditions, precipitate appeared as a white spot against the black background, and was scored based on the fraction of the second buffer condition drop covered by precipitate (scale of 0 to 4, with 0 for no precipitate and 4 for precipitate completely covering the drop). The results are shown in Table 1.

TABLE 1

Microdrop pH screen of GMF-b

| Buffer[a] | Drop No. | pH | Score[b] |
|---|---|---|---|
| Potassium Phosphate | 1 | 5.0 | 2 |
| Potassium Phosphate | 2 | 6.0 | 1.5 |
| Potassium Phosphate | 3 | 7.0 | 1 |
| Potassium Phosphate | 4 | 7.4 | 1 |
| Sodium Phosphate | 5 | 5.5 | 2.5 |
| Sodium Phosphate | 6 | 6.5 | 0.5 |
| Sodium Phosphate | 7 | 7.5 | 0.5 |
| Sodium Acetate | 8 | 4.5 | 3 |
| Sodium Citrate | 9 | 4.7 | 2.5 |
| Sodium Acetate | 10 | 5.0 | 1.5 |
| Sodium Citrate | 11 | 5.5 | 1.5 |
| Cacodylic Acid | 12 | 6.5 | 1.5 |
| Ammonium Acetate | 13 | 7.3 | 2 |
| Imidazole | 14 | 8.0 | 3 |
| Bicine | 15 | 8.5 | 3 |
| Bicine | 16 | 9.0 | 4 |
| MES | 17 | 5.8 | 3 |
| MES | 18 | 6.2 | 2.5 |
| MES | 19 | 6.5 | 2 |
| HEPES | 20 | 7.0 | 1 |
| HEPES | 21 | 8.0 | 1.5 |
| TRIS | 22 | 7.5 | 1 |
| TRIS | 23 | 8.0 | 1.5 |
| TRIS | 24 | 8.5 | 3 |

[a]all buffers are 100 mM;
[b]score is based on the surface of the drop covered by precipitate after 24 hr at room temperature (0 = clear, i.e., fully soluble; 4 = entire drop, i.e., insoluble).

Based upon the pH screening results, it was concluded that (i) sodium phosphate at pH 7.5 was better than the original potassium phosphate buffer, (ii) HEPES at pH 7.0 and TRIS at pH 7.5 were good low ionic strength alternative buffers, and (iii) MES, acetate, and any buffer with pH $\geq$8.5 were poor choices.

A stabilizer screen was carried out using the most solubilizing buffer conditions identified in the pH and buffer screen: sodium phosphate at pH 7.5 and HEPES at pH 7.0. 24 drops were screened, each first buffer condition drop contained 2 ul of GMF-b (9.9 mg/ml in 10 mM potassium phosphate) combined with 2 ul of reservoir solution. The results are shown in Table 2 below.

TABLE 2

Microdrop stabilizer screen of GMF-β

| Stabilizers Screened | Results |
|---|---|
| 25 mM, 50 mM, 100 mM sodium phosphate | no concentration effect |
| 10 mM beta mercaptoethanol | no improvement in solubility |
| 5% and 10% glycerol | no improvement in solubility |

TABLE 2-continued

Microdrop stabilizer screen of GMF-β

| Stabilizers Screened | Results |
|---|---|
| HEPES at pH 7.0 | less soluble than phosphate |
| 2 mM CHAPS | improved solubility |
| 25 mM, 50 mM, 100 mM sodium chloride | no improvement in solubility |

Based upon these results, a new sample of GMF-24 was prepared in 50 mM sodium phosphate at pH 7.4 with 2 mM CHAPS. Using these optimized buffer conditions, the sample was successfully concentrated to 1.3 mM (a four-fold improvement from the initial solubility) and successfully used for NMR spectroscopy.

While I have hereinbefore presented a number of embodiments of this invention, it is apparent that my basic construction can be altered to provide other embodiments which utilize the methods of this invention. Therefore, it will be appreciated that the scope of this invention is to be defined by the claims appended hereto rather than the specific embodiments which have been presented hereinbefore by way of example.

I claim:

1. A process for identifying a buffer condition suitable for determining a biophysical property of a protein, wherein said biophysical property requires said protein to be in solution, comprising the steps of:
   a. providing a first buffer condition comprising a protein and a pH-maintaining reagent, both dissolved in a solvent,
   b. exposing said first buffer condition to a reservoir solution under conditions which modify said first buffer condition to a second buffer condition through vapor diffusion means;
   c. determining if said protein is soluble in said second buffer condition; and
   d. if said protein is soluble in said second buffer condition, evaluate the suitability of said second buffer condition for determining the biophysical property of the protein.

2. The process according to claim 1, wherein said first buffer condition further comprises a stabilizer dissolved in said solvent.

3. The process according to claim 1, wherein the concentration of the protein in said first buffer condition is higher than the concentration of protein in said second buffer condition.

4. The process according to claim 1, wherein the concentration of the protein in said first buffer condition is lower than the concentration of protein in said second buffer condition.

5. The process according to claim 2, wherein said stabilizer is selected from a salt, a reducing agent, glycerol, a detergent, a polyol, an osmolyte, a chaotrope, an organic solvent, an electrostatic reagent, a metal ion, a ligand, inhibitor, cofactor or substrate, a chaperonin, a redox buffer, disulfide isomerase or a protease inhibitor.

6. The process according to claim 1, wherein said biophysical property to be determined is selected from solubility, biological activity, protein aggregation, protein folding and suitability for NMR spectroscopy.

7. The process according to claim 1, wherein the pH of said first buffer condition differs from that of said second buffer condition.

8. The process according to claim 1, wherein in step b), multiple first buffer conditions are exposed simultaneously to the same reservoir solution.

9. The process according to claim 1, wherein in step b), multiple first buffer conditions are exposed simultaneously to multiple reservoir solutions.

* * * * *

UNITED STATES PATENT AND TRADEMARK OFFICE
CERTIFICATE OF CORRECTION

PATENT NO.   : 6,057,159
DATED        : May 2, 2000
INVENTOR(S)  : Christopher A. Lepre It is certified that error appears in the above-identified patent and that said Letters Patent is hereby corrected as shown below:

Column 11,
Line 33, delete "solvent," and substitute therefor -- solvent; --.

Column 1,
Line 46, delete "of" and substitute therefor -- or --.

Column 3,
Line 31, delete "[N,N-bis- (2-hydroxyethyl) -2" and substitute therefor -- [N,N-bis- (2-hydroxyethyl) -2] --.
Line 45, delete "[piperazine" and substitute therefor -- [ (piperazine --.
Line 50, delete "{tris- (hydroxylmethyl-" and substitute therefor -- [tris-(hydroxylmethyl)- --.

Column 4,
Line 4, delete "solvent" to -- solvents --.
Line 43, delete "bilizer" and substitute therefore -- bilizers --.

Column 5,
Line 30, delete "hanging" and substitute therefor -- hanging- --.
Line 31, delete "sitting drop" and substitute therefor -- sitting-drop --.

Column 6,
Line 39, delete "ul)," and substitute therefor -- u1), and substitute therefor -- $\mu$1), --.

Column 8,
Line 4, delete "sitting drop" and substitute therefor -- sitting-drop --.
Line 5, delete "sandwich drop" and substitute therefore -- sandwich-drop --.
Line 40, delete "three dimensional" and substitute therefor -- three-dimensional --.
Line 47, insert -- be -- after "can".
Line 50, delete "be also be" and substitute therefore -- also be --.

UNITED STATES PATENT AND TRADEMARK OFFICE
CERTIFICATE OF CORRECTION

PATENT NO. : 6,057,159
DATED : May 2, 2000
INVENTOR(S) : Christopher A. Lepre

It is certified that error appears in the above-identified patent and that said Letters Patent is hereby corrected as shown below:

Column 10,
Line 41, insert -- area -- after "surface".

Signed and Sealed this

Ninth Day of October, 2001

Attest:

*Attesting Officer*

NICHOLAS P. GODICI
*Acting Director of the United States Patent and Trademark Office*

UNITED STATES PATENT AND TRADEMARK OFFICE
CERTIFICATE OF CORRECTION

PATENT NO.   : 6,057,159
DATED        : May 2, 2000
INVENTOR(S)  : Christopher A. Lepre It is certified that error appears in the above-identified patent and that said Letters Patent is hereby corrected as shown below:

Column 1,
Line 46, delete "of" and substitute therefor -- or --.

Column 3,
Line 31, delete "[N,N-bis- (2-hydroxyethyl) -2" and substitute therefor -- [N,N-bis- (2-hydroxyethyl) -2] --.
Line 45, delete "[piperazine" and substitute therefor -- [ (piperazine --.
Line 50, delete "{tris- (hydroxylmethyl-" and substitute therefor -- [tris- (hydroxylmethyl)- --.

Column 4,
Line 4, delete "solvent" to -- solvents --.
Line 43, delete "bilizer" and substitute therefor -- bilizers --.

Column 5,
Line 30, delete "hanging" and substitute therefor -- hanging- --.
Line 31, delete "sitting drop" and substitute therefor -- sitting-drop --.

Column 6,
Line 39, delete "ul)," and substitute therefor -- µl), --.

Column 8,
Line 4, delete "sitting drop" and substitute therefor -- sitting-drop --.
Line 5, delete "sandwich drop" and substitute therefor -- sandwich-drop --.
Line 40, delete "three dimensional" and substitute therefor -- three-dimensional --.
Line 47, insert -- be -- after "can".
Line 50, delete "be also be" and substitute therefor -- also be --.

Column 10,
Line 41, insert -- area -- after "surface".

UNITED STATES PATENT AND TRADEMARK OFFICE
CERTIFICATE OF CORRECTION

PATENT NO. : 6,057,159
DATED : May 2, 2000
INVENTOR(S) : Christopher A. Lepre

It is certified that error appears in the above-identified patent and that said Letters Patent is hereby corrected as shown below:

Column 11,
Line 33, delete "solvent," and substitute therefor -- solvent; --.

This certificate supersedes Certificate of Correction issued October 9, 2001.

Signed and Sealed this

Twenty-fifth Day of February, 2003

JAMES E. ROGAN
*Director of the United States Patent and Trademark Office*